United States Patent
Bacher

(10) Patent No.: US 6,706,056 B2
(45) Date of Patent: Mar. 16, 2004

(54) MEDICAL, ESPECIALLY SURGICAL, INSTRUMENT

(75) Inventor: Uwe Bacher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 130 days.

(21) Appl. No.: 10/033,757

(22) Filed: Dec. 28, 2001

(65) Prior Publication Data

US 2002/0147460 A1 Oct. 10, 2002

Related U.S. Application Data

(63) Continuation of application No. PCT/EP00/06006, filed on Jun. 28, 2000.

(30) Foreign Application Priority Data

Jul. 1, 1999 (DE) .......................................... 199 30 426

(51) Int. Cl.[7] .............................................. A61B 17/28
(52) U.S. Cl. ...................................................... 606/208
(58) Field of Search ................................ 606/205, 207, 606/208, 210, 206, 167, 170, 171, 174

(56) References Cited

U.S. PATENT DOCUMENTS

| | | | |
|---|---|---|---|
| 4,309,042 A | 1/1982 | Fauth et al. .................... 279/75 |
| 4,403,959 A | 9/1983 | Hatakeyama ................ 433/126 |
| 4,577,875 A | 3/1986 | Miyakawa ..................... 279/75 |
| 5,125,835 A | 6/1992 | Young .......................... 433/80 |
| 5,398,946 A | 3/1995 | Quiring ........................ 279/30 |
| 5,562,655 A | * 10/1996 | Mittelstadt et al. .......... 606/208 |
| 5,735,874 A | * 4/1998 | Measamer et al. ........... 606/208 |
| 5,893,851 A | 4/1999 | Umber et al. ................. 606/80 |

FOREIGN PATENT DOCUMENTS

| | | |
|---|---|---|
| DE | 2033 247 | 3/1971 |
| DE | 81 36 066.5 | 4/1982 |
| DE | 39 34 610 A1 | 4/1991 |
| DE | 94 18 094.6 | 2/1995 |
| DE | 43 41 736 A1 | 6/1995 |
| DE | 195 14 098 A1 | 10/1996 |
| EP | 0 596 272 A1 | 5/1994 |
| EP | 0 700 662 A1 | 3/1995 |
| EP | 0 788 764 A1 | 8/1997 |

* cited by examiner

Primary Examiner—Kevin T. Truong
(74) Attorney, Agent, or Firm—St. Onge Steward Johnston & Reens LLC

(57) ABSTRACT

The present invention relates to a medical instrument, especially for use in surgery, comprising two parts which can be joined to each other; a coupling sleeve which is joined to one of the two parts of said instrument, and a coupling shank which is formed on the other part of the instrument and can be fixed inside the coupling sleeve, where said coupling sleeve and the coupling shank can be joined to each other in a non-positive fit by at least one coupling element arranged inside a guide cage and where the said coupling element is principally slidable in an axial direction only and the coupling is provided with only one spring element. In order to produce a simple and cost-effective medical instrument, the coupling element is brought into contact with oblique contact members of the coupling sleeve and the coupling shank, and the angle (alpha) formed between the center axis of the coupling sleeve and the oblique contact member of the coupling sleeve is greater than the angle (beta) formed between the center axis of the coupling shank and the oblique contact member of the coupling shank.

13 Claims, 6 Drawing Sheets

MEDICAL, ESPECIALLY SURGICAL, INSTRUMENT

This application is a continuation of pending International Application PCT/EP00/06006 filed on Jun. 28, 2000, which designates the United States and claims priority from German Application 199 30 426.2 filed on Jul. 1, 1999.

FIELD OF THE INVENTION

The invention relates to a medical instrument, especially for use in surgery, comprising two parts which can be joined to each other by means of a coupling, a coupling sleeve which is joined to one of the two parts of said instrument, and a coupling shank which is formed on the other part of the instrument and can be fixed inside the coupling sleeve, where the coupling sleeve and the coupling shank can be joined to each other in a non-positive fit by at least one coupling element arranged inside a guide cage, and where the coupling element can be moved in an essentially axial manner only, and where the coupling is provided with only one spring element.

BACKGROUND OF THE INVENTION

A medical instrument of this type is, for instance, known from DE-A1 43 41 736. In this known instrument, the coupling shank is fixed on the grip, or on the sleeve, by means of a ball used as coupling element, which when engaged is inserted into a recess of the coupling shank. Thanks to this structure, the entire axial force applied on the instrument and by the instrument must be transmitted by means of the ball used as coupling element. This results in extreme pressure on the recess of the coupling shank as well as a transverse loading of the ball on two closely adjacent points on the spherical surface.

Another medical instrument is, for instance, known from DE-A1 195 14 098 submitted by the applicant. In this instrument designed in the form of a tube shank instrument, the two parts of the instrument are fixed together by means of a recess formed in the coupling shank which is inserted into the coupling sleeve. The coupling element designed in the form of a ball is inserted, in engaged position, into said recess under compressive load of a first spring. To release this connection, the coupling sleeve is designed as a turn sleeve which can be pivoted around the longitudinal axis of the tube shank instrument. A second spring, i.e. a torsion spring, is arranged inside the turn sleeve and counteracts the rotation. Although the coupling of this medical instrument secures a secure joining of both parts of the instrument to one another, the diameter of said instrument is large, partly because of the design of the turn sleeve, so that an instrument of this type is too big and awkward for use in the HNO area, for instance. In addition, the manufacture of the coupling for said instrument is quite expensive because of the use of the two springs, among other reasons.

Other medical instruments comprising rapid couplings are known, for instance, from DE-A1 39 34 610, U.S. Pat. No. 4,403,959 and from U.S. Pat. No. 4,577,875. The disadvantage of all these instrument couplings is that, first, they have a large diameter and, second, they require at least two spring elements in order to ensure a joining of both parts of the instrument parts to one another without vacant space. Because of this type of structure, the known medical instruments comprising rapid couplings are quite costly.

Because of this state of the art, it is the objective of the present invention to provide a medical instrument of the aforementioned type, which ensures a joining of both parts of the instrument to one another that is essentially free from play, and whose structure is simple and cost-effective as well as slender in design.

The solution to this objective by the invention is characterized in that the coupling element abuts onto oblique contact members of coupling sleeves and coupling shank, and the angle (alpha) between the center axis of the coupling sleeve and the oblique contact member of said coupling sleeve is larger than the angle (beta) between the center axis of the coupling shank and the oblique contact member of said coupling shank.

In the instrument in accordance with the present invention, the force generated by inserting the shank into the coupling sleeve is absorbed by the contact members. On the other hand, the coupling is automatically engaged because of the different inclination of the oblique contact member when pulling out the shank. The ball is compressed in its entirety over two nearly opposite points on the spherical surface and is brought into contact with the oblique contact members of the coupling sleeve and coupling shank, resulting in minimal wear and tear. This structure of the coupling comprising both oblique contact members and the coupling element arranged between said oblique contact members facilitates a simple compensation of manufacturing tolerances, since no precise engagement position is defined in contrast to the technique of DE 43 41 736 A1. Therefore, the coupling in accordance with the present invention facilitates the transmission of great forces and momentum, and simultaneously ensures secure linkage of the coupling elements.

In addition, the invention calls for the attachment of a slider on the outside surface of the coupling sleeve, where said slider is adjustable in the axial direction of said coupling sleeve and engaged with the guide cage for at least one coupling element. At least one coupling element is slidable by means of this slider and also engages with the oblique contact member of the coupling shank. The use of the slider which can move in the axial direction of the coupling sleeve facilitates a considerable reduction of the diameter of the coupling in comparison with the couplings of the instruments defined by current technology. Moreover, the slider is simple in construction, which in turn lowers the cost of manufacture of a medical instrument in accordance with the invention.

In a practical embodiment of the present invention, it is proposed that the slider and the guide cage are joined together by clamping or in a non-positive fit for at least one coupling element over at least one retaining member. The axial movement of the slider is transmitted over said retaining member to the guide cage of the coupling element in such a way that the shifting of the slider against the force of a compression spring under compressive load brings the coupling element into an engaged position so that at least one coupling element released from the oblique contact member of the coupling shank can be engaged.

In order to avoid a twisting of both parts of the instrument against one another, the present invention proposes a mounting of a protection against torsion between both instrument parts.

In accordance with a first practical embodiment of the present invention, the protection against torsion is designed as a pivot arranged in one of the instrument parts, which engages in a corresponding groove of the other instrument part.

In accordance with a second embodiment of the present invention, the pivot in one of the two instrument parts can be engaged in one of several grooves of the other instrument part. This arrangement makes it possible to secure the instrument parts to one another at various angles.

In accordance with another embodiment of the present invention, the instrument parts can be joined to one another at various angles because the protection against torsion is designed in the form of an engagement mechanism acting between the instrument parts.

A particularly great freedom of play between both parts of the instrument to be joined together can be obtained if the coupling shank over its peripheral area is in contact with two contact members located on the inner side of the coupling sleeve, where the distance between said contact members is several times greater than the diameter of said coupling shank as seen in the axial direction of the coupling shank. Furthermore, the greater distance between the contact members prevents the high maximum torque to the other part of the instrument that occurs with known instruments.

In accordance with a practical embodiment of the present invention, one of the two contact members is conical. It is also proposed, in accordance with the invention, For use of an inventive medical instrument as a tube shank instrument, one part of the instrument has a handle comprising a fixed handle part and a pivotal handle part arranged opposite to said fixed handle part. The other instrument part is provided with a push/pull rod arranged in the coupling shank provided for use of a medical gripping instrument.

With this refinement, the medical instrument in accordance with the present invention is characterized in that a retaining member is arranged on the proximal end of said push/pull rod which can be fixed in a triggering element that is slidable in the axial direction of said handle part.

In accordance with a preferred embodiment of the present invention, the retaining member on the proximal end of the push/pull rod is designed as a ball which engages in a complementary ball socket in the manipulating element.

Finally, the present invention proposes a pivot-groove control between the pivotal grip of the handle part and the manipulating element axially slidable in said handle part, and which is used for shifting the push/pull rod.

BRIEF DESCRIPTION OF THE DRAWINGS

The following description of the attached illustrations defines the features and advantages, which are explained by means of an example of the preferred embodiment of a medical instrument according to the present invention. The illustrations are as follows.

FIG. 1b An enlarged detail view of the depiction in FIG. 1a.

FIG. 2b An enlarged detail view of the depiction shown in FIG. 2a.

DETAILED DESCRIPTION OF THE DRAWINGS

Figure 1A:
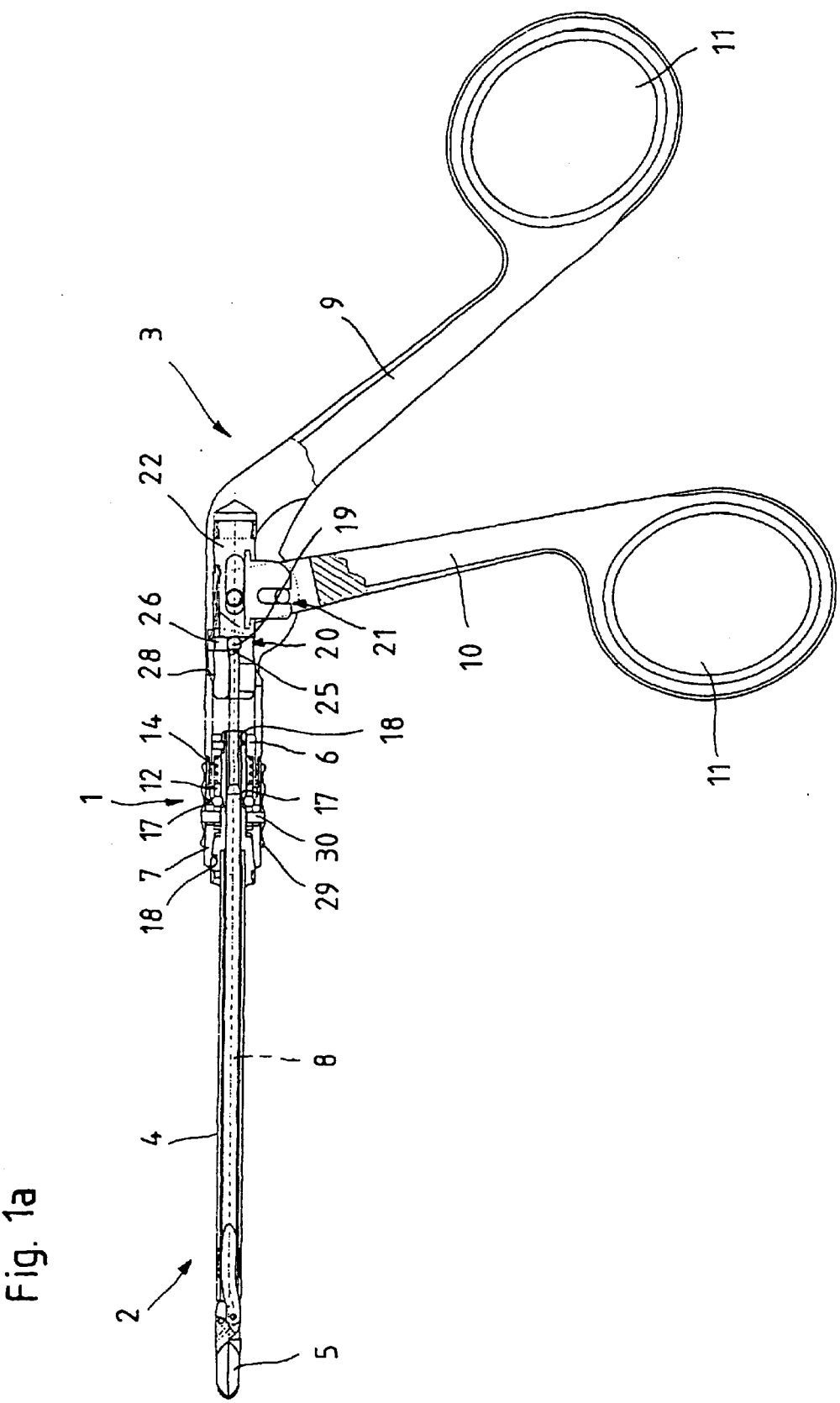
FIG. 1a A partially sectional side view of the medical instrument in accordance with the present invention comprising a closed gripping instrument.

The medical instrument shown in the figures relates to a tube shank instrument, that is, a gripping pincer. The said instrument comprises two parts connected over a coupling 1, that is, the gripping instrument 2 and the handle 3, which are shown individually in FIG. 3.

In the depicted embodiment shows the gripping instrument comprises a longitudinal shank 4 on whose distal end the actual pincer part 5 is arranged. To connect with the handle 3, the proximal end of the shank 4 of said gripping instrument 2 is designed as a coupling shank 6 which forms the coupling 1 together with the coupling sleeve 7 arranged on the distal end of the handle 3.

The pincer part 5 is moved by means of a push/pull rod 8 arranged inside the shank 4 which can be shifted by means of the handle 3.

The said handle 3 comprises a fixed handle part 9 and a pivotal handle part 10 arranged opposite to said fixed handle part 9. To grip and use the handle 3, lugs 11 are provided on the free ends of said handle parts 9, 10.

Figure 1B:
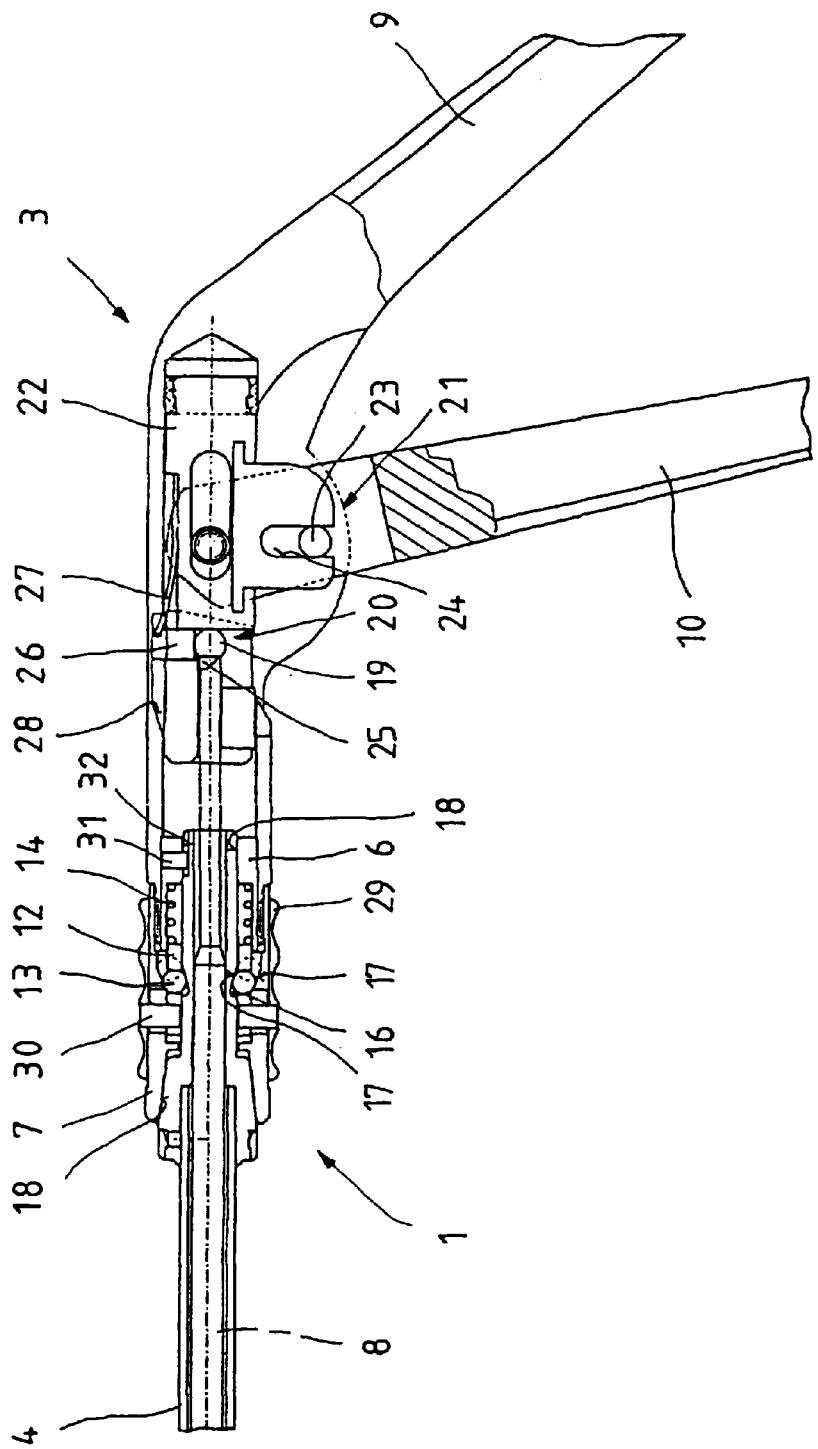
Figure 2A:
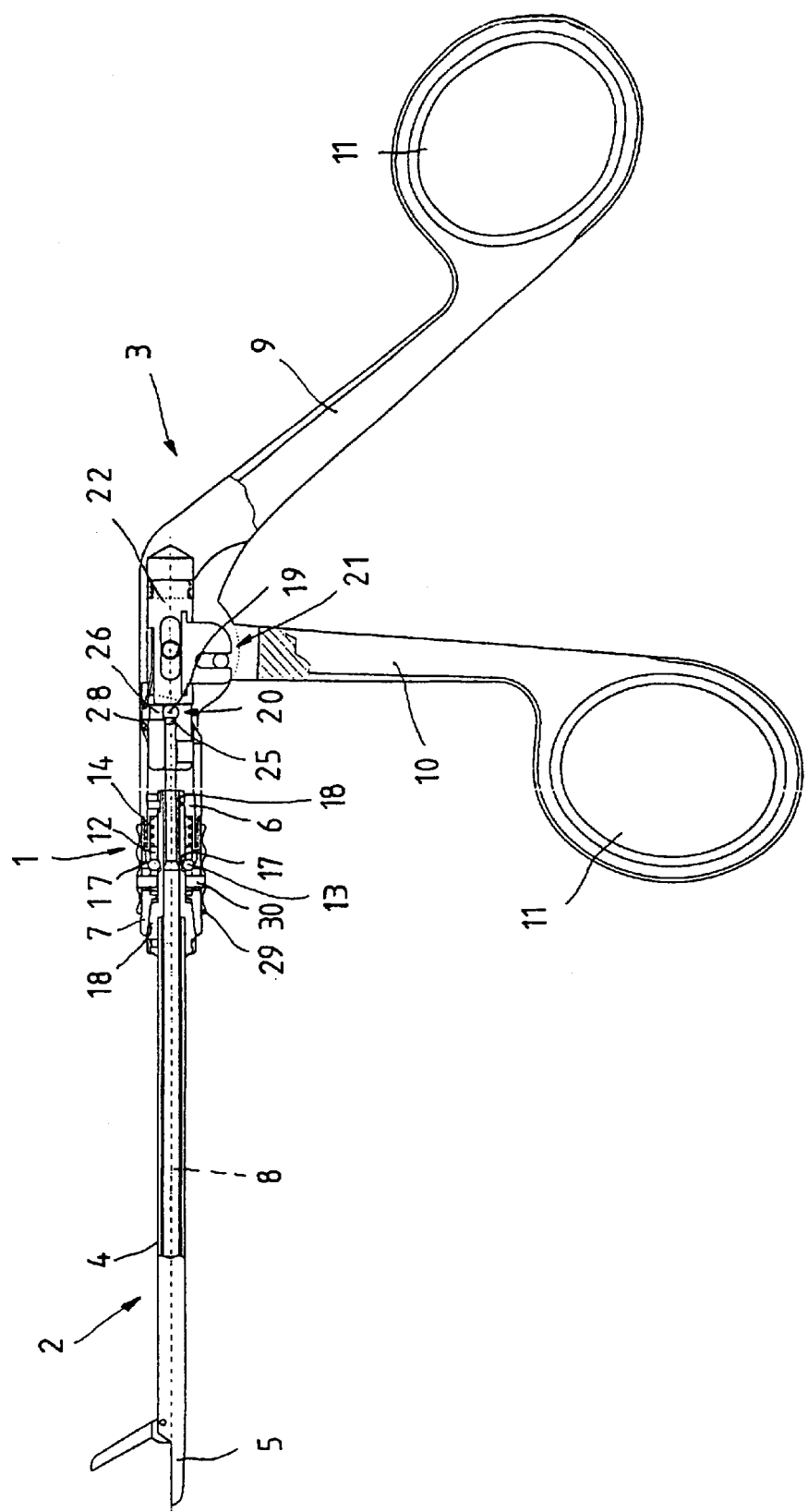
FIG. 2a A partially sectional side view of the medical instrument shown in FIG. 1a, but with opened gripping instrument.
Figure 2B:
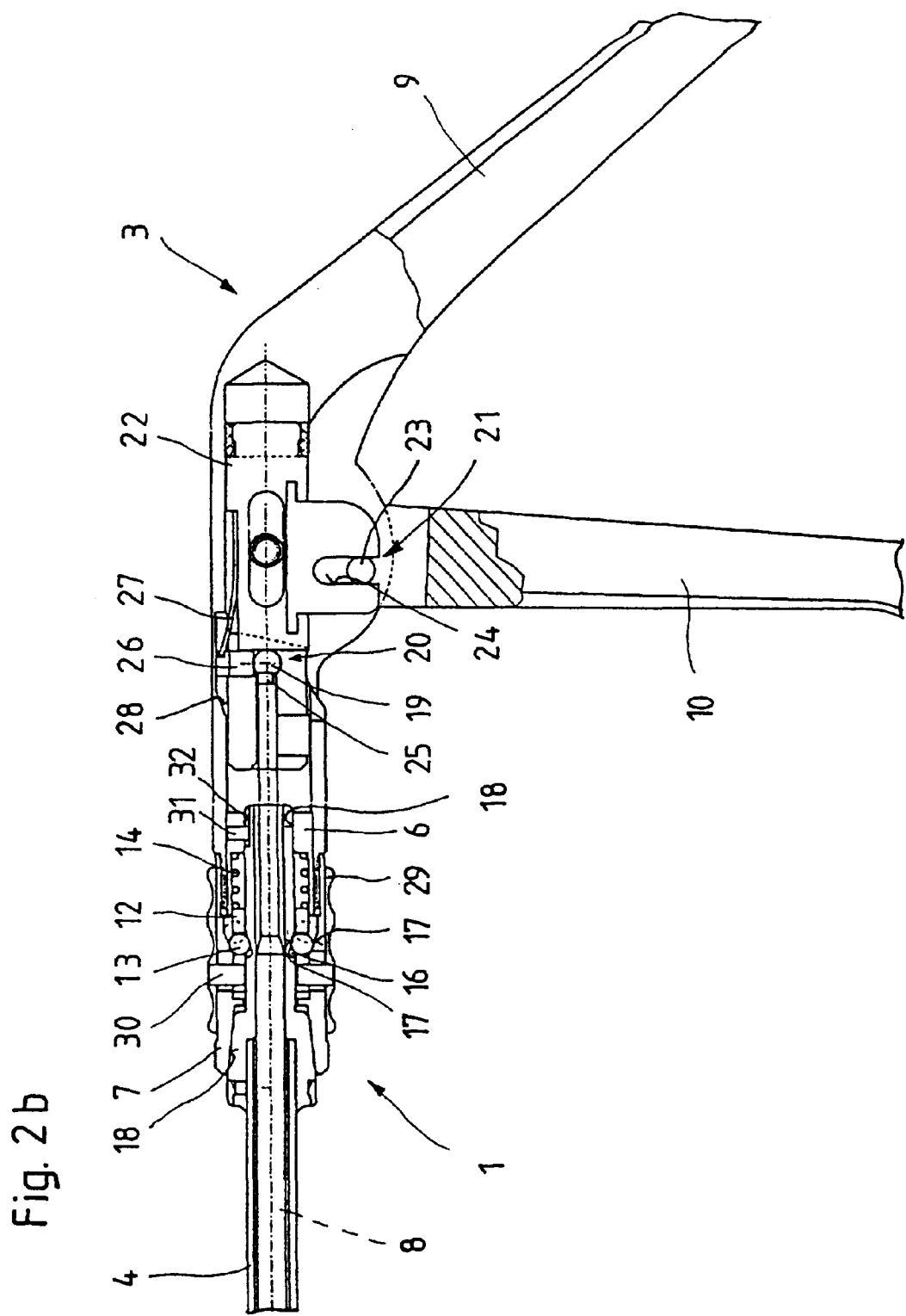
Figure 3:
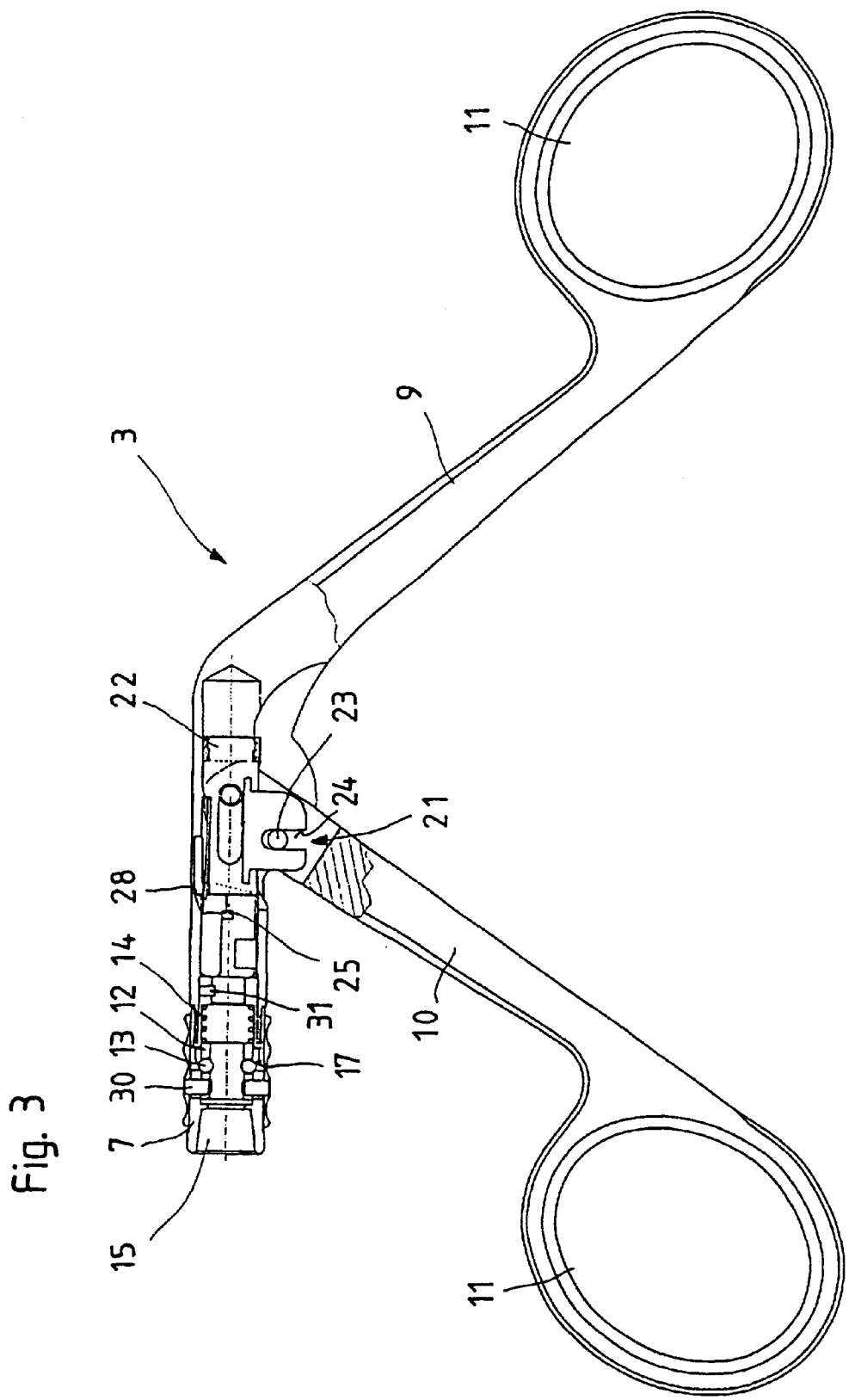
FIG. 3 A partially sectional side view of the handle comprising the coupling sleeve without the second part of the instrument.
Figure 4:
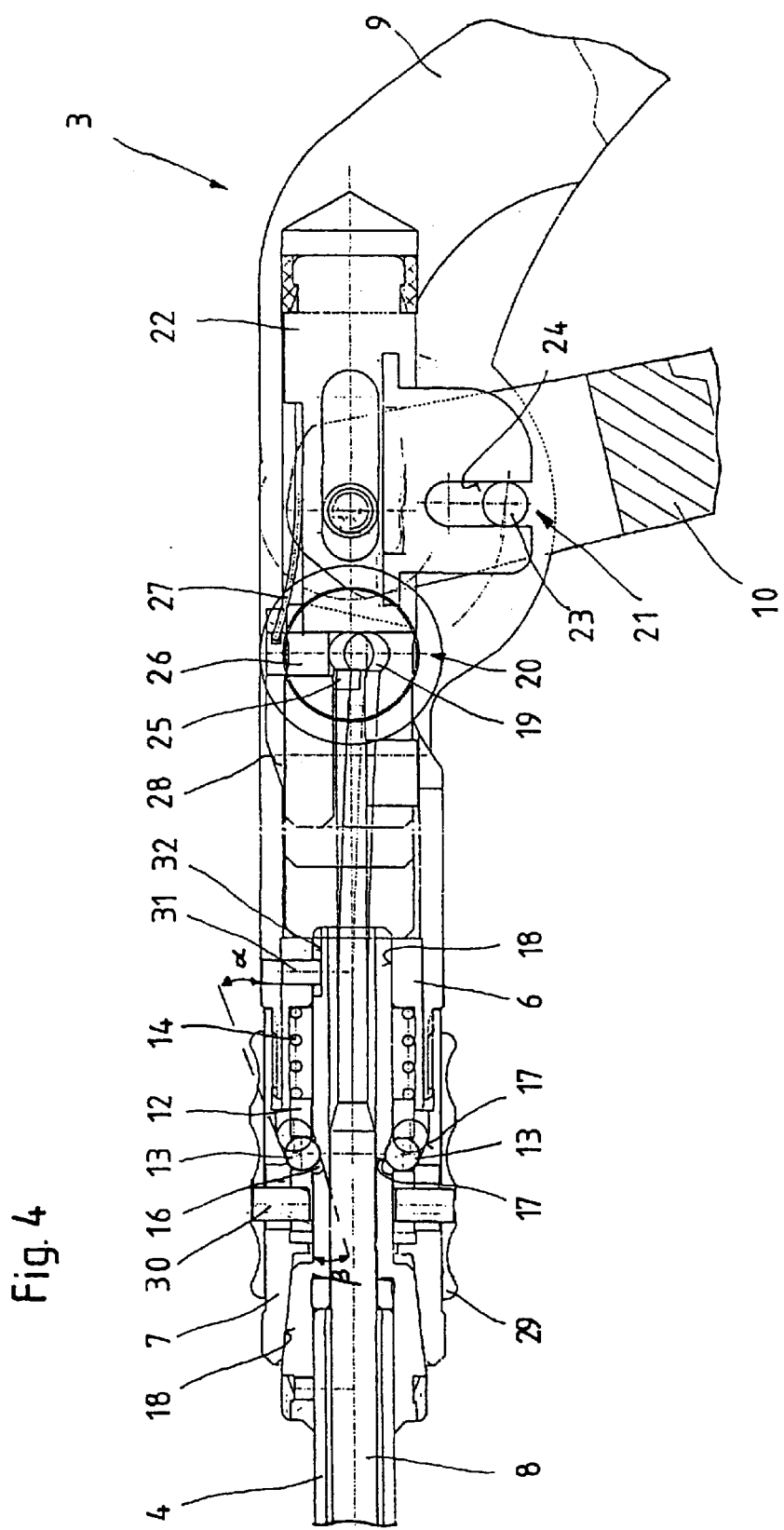
FIG. 4 An enlarged detailed view of the linkage between the coupling sleeve and coupling shank depicting the engagement of the ball on the push/pull rod inside the ball socket.

FIGS. 1b, 2b, 3 and especially FIG. 4 show the structure of the coupling 1 as well as the operating method of the handle 3 and the push/pull rod 8.

As shown in the depicted embodiment, the coupling sleeve 7 connected with the handle 3 comprises a guide cage 12 which can be slid in an axial direction and located on the inner side which is used for inserting the coupling shank 6. The coupling elements 13 designed in form of balls are arranged inside the said guide cage 12. The ring-shaped guide cage 12 is prestressed for the coupling shank 6 by means of a compression spring 14 in the direction of an insertion opening 15 of the coupling sleeve 7. Moreover, the said guide cage 12 has a free inside diameter between the coupling elements 13, which is smaller than the outside diameter of the coupling shank 6, so that the guide cage 12 will be shifted to the proximal end of the handle 3 together with the coupling elements 13 arranged inside said guide cage 12 when the coupling shank 6 is inserted into the coupling sleeve 7. The gripping instrument 2 and handle 3, or the coupling shank 6 and the coupling sleeve 7, respectively, are engaged with one another by a circular recess 16 on the outer surface of the coupling shank 6, where the coupling elements 13 are entered into as soon as the coupling shank 6 has been inserted sufficiently into the coupling sleeve 7.

In the engaged position of the coupling elements 13, said coupling elements designed as balls are brought into contact with oblique contact members 17 which are arranged on the inner side of the coupling sleeve on the one hand, and arranged within the range of the recess 16 in the coupling shank 6 on the other hand. The inclinations of the oblique contact members 17 to the center axis of the coupling sleeve 7 and the coupling shank 6 are designed so that the angle (alpha) between said center axis of the coupling sleeve 7 and the oblique contact member 17 of the coupling sleeve 7 is greater than the angle (beta) between the center axis of the coupling shank 6 and the oblique contact member 17 in the recess 17. Because of the angular difference, alpha is greater than beta, and the pre-stressing of the coupling elements 13 on the compression spring 14 arranged above the guide cage 12, both structural parts 2 and 3 to be connected with one another are constantly under pressure on the conical contact member 18. This in turn results in an especially secure linking, free from play, of both structural parts 2 and 3 to one another.

As particularly shown in FIG. 4, the coupling shank 6 inside the coupling sleeve 7 is brought into contact with two contact members 18 whose distance from one another is several times greater than the outside diameter of the coupling shank 6. This distance between the contact members results in a reduced freedom from play between the gripping instrument 2 and the handle 3, which also applies to the instruments in accordance with the current embodiment. Under pressure when the gripping device 5 is closed, the force applied onto the contact members 18 is so great that no torsion is possible between the handle 3 and the gripping instrument 2.

In order to fix the push/pull rod of the handle 3, said push/pull rod comprises a ball 19 on its proximal end which can be fixed in a ball socket 20 of said handle 3. The gripping device 5 can be shifted from the closed position shown in FIG. 1a into the opened position by means of a pivot-groove control 21 mounted between the pivotal handle part 10 of the handle 3 and a manipulating element 22 which is arranged inside the handle 3 so that it can be slid in the axial direction of said handle 3. The depicted embodiment shows that the pivot 33 of the pivot-groove control 23 is connected with the pivotal handle part 10, whereas the groove 24 is formed inside the manipulating element 22.

When the ball 19 is engaged within the ball socket 20, the said ball is inserted in an engagement element 25 and is brought into contact with an unlocking bolt 26 which is prestressed by means of a spring element 27 and away from the ball 19. The manipulating element 22 can be proceeded along a control cam 28 on the inner side of the handle 3 by shifting said manipulating element 22 by means of the pivotal handle part 10.

The locking and unlocking of the instrument parts 2 and 3 by means of the coupling 1 as well as the manipulation of the gripping device 5 by the handle 3 is performed as follows.

To form the assembled medical instrument shown in FIG. 1a and FIG. 2a, the gripping instrument 2 is inserted with the proximal end of the shank 4 of said gripping instrument 2 into the coupling sleeve 7 of the handle 3 shown in FIG. 3. Since the outside diameter of the coupling shank 6 is larger than the free inside diameter between the coupling elements 13 arranged inside the ring-shaped guide cage 12, the said guide cage 12 along with the coupling elements 13 inside said guide cage 12 is pressured against the force of the compression spring 14 and away from the insertion opening 15 of the coupling sleeve 7.

When the coupling shank 6 is inserted into the coupling sleeve 7.

The guide cage 12 is pressed back until the recess 16 formed on the surface of the coupling shank 6 reaches the area of the coupling elements 13. At this moment, the coupling elements 13 are inserted into the circular recess 16, thus making it possible again for the compression spring 14 to press the guide cage 12 in the direction of the insertion opening 15 of the coupling sleeve 7. This procedure is repeated until the coupling elements 13 are brought into contact with the slanting surfaces 17 of the coupling sleeve 7 and of the recess 16. Because of the permanent pressure applied by the compression spring 14, the angular difference between the oblique contact members 17 results in a secure fixing, free from play, of both parts 2 and 3 of the instrument that are to be joined to one another.

To unlock the linkage, a slider 29 is arranged on the outside of the coupling sleeve 7 which can be slid in the axial direction. By means of said slider 29, the guide cage 12 can be moved by a retaining member 30 against the force exerted by the compression spring 14.

When shifting the slider 29 to the proximal end of the handle 3, the guide cage 12 together with the coupling elements 3 will be moved along because of the retaining member 30. Because of the angular difference between the contact surfaces of the slanting surfaces 17, the distance between both contact surfaces is increased again until the coupling shank 6 can be removed again from the coupling sleeve 7. Thus the coupling element 13 is disengaged from the recess 16 so that the coupling linkage is interrupted.

In addition, as shown in FIG. 4, upon insertion of the coupling shank 6 into the coupling sleeve 7, the push/pull rod 8 arranged inside the shank 4 of the gripping instrument 2 is bent downward. The said push/pull rod 8 is bent until the ball 19 of the push/pull rod 8 has overcome the engagement element 25 when inserting the coupling shank 6 into the coupling sleeve 7, and until said ball 19 is fixed in the ball socket 20.

The gripping device 5 is manipulated by the pivot-groove control 21 when the pivotal handle part 10 is moved. This enables a shifting of the manipulating element 22 adjacent to the ball 19 in the axial direction within the handle 3.

To avoid a torsion of the handle 3 and the gripping instrument 2 against one another, a protection against torsion is arranged between both parts 2, 3 of the instrument which comprises a pivot 31 formed in the handle 3 as shown by the depicted example of the embodiment. The said pivot 31 is inserted into an appropriately formed groove 32 in the coupling shank 6.

Apart from the defined possibility of connecting the instrument parts 2, 3 in a fixed manner and protected against torsion, the said parts 2, 3 can also be fixed to one another in various angular positions by means of an engagement mechanism, for example (not shown).

As shown in the figures, the construction of the medical instrument defined herein allows a slender type of construction with a small outside diameter, and thus an instrument of this type can also be used for surgery in HNO areas.

| Key to illustrations | |
|---|---|
| 1 coupling | |
| 2 | gripping instrument |
| 3 | handle |
| 4 | shank |
| 5 | gripping device |
| 6 | coupling shank |
| 7 | coupling sleeve |
| 8 | push/pull rod |
| 9 | fixed handle part |
| 10 | pivotable handle part |
| 11 | lug |
| 12 | guide cage |
| 13 | coupling element |
| 14 | compression spring |
| 15 | insertion opening |
| 16 | recess |
| 17 | oblique contact member (alpha angle) |
| 18 | contact member (beta angle) |
| 19 | ball |
| 20 | ball socket |
| 21 | pivot-groove control |
| 22 | manipulating element |
| 23 | pivot |
| 24 | grooved hole |
| 25 | engaging element |
| 26 | unlocking bolt |
| 27 | spring element |
| 28 | control cam |

-continued

Key to illustrations

| 29 | slider |
| 30 | retaining member |
| 31 | pivot |
| 32 | groove |

What is claimed is:

1. Medical instrument, especially for use in surgery, comprising two parts which can be joined to each other; with a coupling sleeve which is joined to one of the two parts of said instrument, and a coupling shank which is formed from the other part of the instrument and can be fixed inside the coupling sleeve, where said coupling sleeve and the coupling shank can be joined to each other in a non-positive fit by at least one coupling element arranged inside a guide cage and where the said coupling element is principally slidable in an axial direction only and the coupling is provided with only one spring element, characterized in that the coupling element is in contact with oblique contact members of the coupling sleeve and the coupling shank, and that the angle (alpha) between the center axis of the coupling sleeve and the oblique contact member of said coupling sleeve is larger than the angle (beta) formed between the center axis of the coupling shank and the oblique contact member of said coupling shank.

2. Medical instrument in accordance with claim 1, characterized in that the outside of the coupling sleeve is provided with a slider, which is adjustable in an axial direction and which is connected at least in a non-positive fit with the guide cage for at least one coupling element, when the at least one coupling element is disengaged from the oblique contact member of the coupling shank, it can be shifted by means of said slider.

3. Medical instrument in accordance with claim 2, characterized in that the slider and the guide cage are joined together by clamping and/or in a non-positive fit by means of at least one retaining member.

4. Medical instrument in accordance with claim 3, characterized in that a protection against torsion has been provided in order to prevent a twisting of both parts of the instrument against one another.

5. Medical instrument in accordance with claim 4, characterized in that the protection against torsion is designed in the form of one of the pivots arranged within one of the parts of the instrument, which engages into a corresponding groove of the other part.

6. Medical instrument in accordance with claim 4, characterized in that the protection against torsion is designed in form of one of the pivots arranged within one of the parts of the instrument, which can be engaged in one of several grooves of the other instrument part.

7. Medical instrument in accordance with claim 4, characterized in that the protection against torsion is designed as an engagement mechanism between the instrument parts.

8. Medical instrument in accordance with claim 7, characterized in that the coupling shank, over its peripheral area, is in contact with two contact members on the inside surface of the coupling sleeve the distance between the contact members is several times the diameter of the coupling shank when seen in axial direction of the coupling shank.

9. Medical instrument in accordance with claim 8, characterized in that one of the two contact members is conical.

10. Medical instrument in accordance with claim 8, characterized in that one of the two contact members is cylindrical.

11. Medical instrument in accordance with claim 10, characterized in that one part of the instrument is formed as a handle part provided with a fixed grip as well as a pivotal grip part that can pivot from the fixed grip part whereas the other part of the instrument comprises a push/pull rod arranged inside the coupling shank in order to activate a medical gripping instrument, characterized in that a retaining member is arranged on the proximal end of said push/pull rod which can be fixed in a manipulating element that is slidable in axial direction of said handle part.

12. Medical instrument in accordance with claim 11, characterized in that the retaining member on the proximal end of the push/pull rod is designed in form of a ball which engages in a complementary ball socket in the manipulating element.

13. Medical instrument in accordance with claim 11, characterized in that a pivot-groove control is formed between the pivotal grip of the handle part and the manipulating element axially slidable in said handle part, and which is used for shifting the push/pull rod.

\* \* \* \* \*